United States Patent
Adam et al.

(10) Patent No.: US 6,695,958 B1
(45) Date of Patent: Feb. 24, 2004

(54) ELECTROCHEMICAL SENSOR

(75) Inventors: Stefan Adam, Steinfurt (DE); Michael Borchardt, Neuenkirchen (DE); Christoph Diekmann, Munster (DE); Ralf Steinkuhl, Munster (DE)

(73) Assignee: Institut fur Chemo-und Biosensorik Munster E.V., Munster (DE)

( * ) Notice: Subject to any disclaimer, the term of this patent is extended or adjusted under 35 U.S.C. 154(b) by 0 days.

(21) Appl. No.: 09/331,128

(22) PCT Filed: Dec. 18, 1997

(86) PCT No.: PCT/DE97/02960
§ 371 (c)(1),
(2), (4) Date: Jun. 14, 1999

(87) PCT Pub. No.: WO98/28614
PCT Pub. Date: Jul. 2, 1998

(30) Foreign Application Priority Data

Dec. 20, 1996 (DE) .......................... 196 53 436

(51) Int. Cl.[7] .............................. G01N 27/327
(52) U.S. Cl. ............... 204/403.01; 204/403.06; 204/403.07; 204/403.09; 204/403.1; 204/403.11; 204/415; 204/416
(58) Field of Search .............. 204/403.01, 416, 204/418, 419, 415, 403.06, 403.07, 403.09, 403.1, 403.11

(56) References Cited

U.S. PATENT DOCUMENTS

| | | | | |
|---|---|---|---|---|
| 4,053,381 A | * | 10/1977 | Hamblen et al. | |
| 5,108,564 A | * | 4/1992 | Szuminsky et al. | 204/403 |
| 5,385,846 A | * | 1/1995 | Kuhn et al. | |
| 5,437,999 A | * | 8/1995 | Diebold et al. | 204/403 |
| 5,468,374 A | * | 11/1995 | Knoll | |
| 5,538,620 A | * | 7/1996 | Nikolskaja | 204/415 |
| 5,783,056 A | * | 7/1998 | Hampp et al. | |
| 5,981,203 A | * | 11/1999 | Meyerhoff et al. | |

FOREIGN PATENT DOCUMENTS

| | | | |
|---|---|---|---|
| DE | 41 37 261 | | 5/1993 |
| EP | 0266432 | * | 5/1988 |
| EP | 0351891 | * | 1/1990 |
| EP | 0603154 | * | 12/1993 |
| EP | 0592805 A2 | * | 4/1994 |
| JP | 60244853 | * | 12/1985 |
| JP | 61002060 | * | 1/1986 |
| WO | 98/35225 | * | 8/1998 |

OTHER PUBLICATIONS

Search Report for DE 196 53 436 Aug. 13, 1998.

* cited by examiner

*Primary Examiner*—T. Tung
(74) *Attorney, Agent, or Firm*—Leydig, Voit & Mayer, Ltd.

(57) ABSTRACT

The invention relates to a sensor for detecting substance concentration or activity or for determining the presence of substances based on electrochemical reactions. The electrochemical sensor comprises an electrode with surfaces inside the electrode, wherein electrochemical detection reactions occur. Said sensor guarantees high flow densities and is suitable for miniaturization. A substance-recognizing agent is advantageously placed in the electrode in contact with the inner surfaces. This enables not only short response times and long service life but also measurements with excellent linearity.

19 Claims, 7 Drawing Sheets

ELECTROCHEMICAL SENSOR

The invention relates to a sensor for determining material concentrations, activities or for material detection on the basis of electrochemical reactions.

A structure often used in electrochemical sensors consists of a flat support, on which is arranged a flat detection electrode. This electrode is in contact with the sample medium. Certain materials, in the case of platinum electrodes for example hydrogen peroxide, may be detected electrochemically as a result of electrochemical reactions on the electrode surface.

The disadvantage of sensor arrangements of this type is the comparatively small electrode surface and the often low current densities resulting therefrom. Particularly in the course of advancing miniaturization, the surface dimensions of flat electrodes required to achieve sufficiently high current densities are often an insurmountable limit to smaller sensor structural shapes.

The flat sensor electrode is often in contact with a material-recognizing substance in the form of a thin membrane. Materials which may be detected electrochemically at the electrode are formed in the membrane due to a specific detection reaction.

A thin membrane guarantees short diffusion paths from the site of the chemical detection reaction to the electrode and hence short response times. A further advantage of thin membranes is also the avoidance of substrate limitations. In the case of glucose sensors based on glucose oxidase by way of example, there is the danger of oxygen limitation and hence of undesirable non-linearities if the oxygen required for the detection reaction cannot diffuse into the membrane in sufficient quantity.

However, these preferences for thin material-recognizing membranes are partly compensated by adhesion problems due to the often difficult binding of the thin membrane to support and electrode as well as by encapsulation problems. A further disadvantage of thin membranes is the short service life of such sensors, since the comparatively few active membrane components due to the low membrane volume are deactivated or spent in a short time.

The disadvantages just mentioned can be partly avoided by using thicker material-recognizing membranes. However, for thicker membranes there is the problem that long response times for the sensor have to be taken into account due to the long diffusion paths from the site of the chemical reaction to the flat electrode arranged on the support. Furthermore, some of the reacted materials may diffuse from the material-recognizing membrane before detection at the electrode surface, as a result of which the sensitivity is reduced.

A problem with sensor cross-sensitivities often occurs independently of the membrane thickness. The required minimization of such cross-sensitivities is often associated with complex and therefore expensive modifications of conventional sensors.

The object of the invention is to overcome the disadvantages of the state of the art and to provide an electrochemical sensor which can be miniaturized to analyze liquid or gaseous samples, which has short response times and at the same time an increased linear measuring range as well as a long service life, particularly in combination with material-recognizing substances.

For an electrochemical sensor which has at least one electrode having inner hollow cavities into which the material to be determined and/or reacted reaction products may enter, and in which a material-recognizing substance is incorporated in these cavities at least in some regions, advantageously large active detection surfaces can be achieved in the electrode interior even for small external electrode dimensions. A sensor of this type permits realization of high current densities and is particularly suitable also for miniaturization.

Electrodes having inner hollow cavities and consequently having inner surfaces have, in contrast to the traditional flat electrodes, an essentially three-dimensional functionality. Electrodes of this type may have, for example a latticed, reticulated, filamentary or porous structure. It is important that pores, tubes or other hollow cavities having surfaces are present in the interior of the electrode, by means of which the medium to be analyzed and the material to be detected or reacted reaction products of the material to be detected may come into contact with the electrode surface.

The advantages of sensors based on thin-layer membranes and of those based on thick-layer membranes can be combined in a sensor having material-recognizing substance incorporated in the sensor electrode. Consistently short response times are achieved by incorporating the material-recognizing substance in the electrodes, in contrast to thick-layer membrane sensors, independently of the volume of the material-recognizing substances. This is due to the fact that the diffusion path between the site of the chemical reaction and the site of detection of the reaction on the electrode surface is minimal everywhere in the electrode interior. In addition to short response times, high sensitivities can be achieved for amperometric sensors. Since the volume of material-recognizing substance may be increased without considerable losses regarding the response times, a high number of active components are available. The operating period of the sensor is thus considerably extended.

For sensors having material-recognizing substance incorporated in the electrode, it may be advantageous to increase the hollow cavity volumes in favor of incorporating a larger quantity of material-recognizing substance for constant external electrode dimensions. Optimization of sensor service life and sensitivity adapted to the particular application is possible in this manner with consistently short response times.

The essentially three-dimensional sensor electrode is preferably in contact with an electric leakage arranaed on the support and is advantageously composed of several part electrodes (multi-layer structure). In individual or in all part electrodes a specific material-recognizing substance is introduced at least in some areas, for example by capillary forces. Hence the same or different material-recognizing substances may be embedded in different part electrodes. Embedding can often be carried out more simply in a multi-layer structure than for solid electrodes having inner surfaces. A layer electrode which permits simple, layer-like production of individual part electrodes is produced in this manner.

Individual part electrodes may be in electrical contact with one another on the surface so that only one single part matrix needs to be connected to an electric leakage. However, layers of an electrically insulating material may also be arranged between individual part electrodes preferably provided with separate leakages and may be permeable in each case to the material to be detected and to reaction-assisting or reaction-accompanying materials. The part electrodes may also be separated from one another by distancing layers (spacer) which have perforations in a central electrode region. The sandwich construction permits incorporation of different material-recognizing substances in different part electrodes and simultaneously detection of a plurality of materials in a sample solution.

The electrode or part electrodes may consist of a conductive parent substance, for example of metal, or of a conductively coated or metallised, non-conductive parent substance. Suitable conductive parent substances are, for example of metals, such as platinum, silver or gold or of a paste containing carbon and/or one of the afore-mentioned metals. These materials are also suitable as conductive coating for non-conductive parent substances.

Metallic parent substances having inner surface can be produced, for example by etching or by laser treatment. Non-conductive parent substances on the other hand often already have an inner surface from the start. Papers, such as filter paper, paperboards, glass fibers, plastic fibers, textiles, ceramics, mineral materials or materials of vegetable or animal origin, are suitable as non-conductive parent substances for electrodes or part electrodes. Application of metallisation may be effected, for example by sputtering, vaporization using pastes or adhesives or by chemical reaction.

The three-dimensional electrode preferably consists of an insulating parent substance which is surrounded as completely as possible by a very thin layer of a conductor. The production costs of the sensor can be considerably reduced by minimizing the metallisation thickness. Furthermore, it is possible to provide larger surface areas of the parent substance (for example paper webs) with metallisation simultaneously and uniformly. Smaller pieces of it are then used as an electrode or part electrode for the sensors. The production costs can thus be reduced and the signal reproducibility increased.

The material-recognizing substance incorporated in the sensor electrode preferably contains at least one active component, such as enzymes, microbes, bacteria or yeasts, which is preferably immobilized using at least one gel-like or elasticized polymer, such as polyvinyl alcohol, polyvinyl chloride, polyurethane, acrylate or silicone. The material-recognizing substance may be introduced into the electrode parent substance by utilizing capillary action, by vacuum infiltration or by pressure filling.

One or more three-dimensional support cavities receiving the at least one electrode are advantageously arranged on the sensor support or in the support or at least partly in the support of the electrochemical sensor. This at least one support cavity may advantageously be provided with at least one cover. The electrode may thus be encapsulated to provide protection in simple manner and therefore cost-effectively and fixed on the support. This method of encapsulation also avoids the problem of membrane adhesion which often occurs in sensors based on thin-layer membranes.

The support and/or at least one of the covers advantageously has an opening which permits entry of the substance to be detected into the support cavity. The sensor behavior can be optimized by suitable selection of the opening diameter. A small opening diameter, for example reduces the outward diffusion of the substance to be detected and the reacted substance.

Support and cover advantageously consist of a film material based on, for example polyethylene, polyester, polyvinyl chloride, polypropylene, polytetrafluoroethylene, cellulose acetate, silicone or a combination of these materials. The material should be permeable to reaction-assisting or reaction-accompanying materials, but impermeable to the material to be determined. The linear measuring range of the electrochemical sensor is extended in this manner, since depletion of the reaction-assisting or reaction-accompanying materials, that is a substrate limitation, is delayed. Particularly well suited material for support and cover are films, such as heat-sealing films, laminating films, self-adhesive films or sealable films which are joined to one another by melting or adhesion.

An electric leakage arranged on the support and contacting the electrode preferably consists of a metal, such as platinum, silver or gold or of a paste containing carbon and/or one of the afore-mentioned metals, and may be applied to the support by a screen printing process, a silk-screen printing process, a dispensing process, a spraying process, by vaporization or by sputtering.

In addition, a reference electrode or counter-electrode may be arranged on the support to have a reference which is not influenced by the sample matrix or the reaction products, and to facilitate current flow for voltametric measurements. A silver/silver chloride paste by way of example is a suitable material for this electrode.

Measuring electrode as well as reference electrode or counter-electrode may come into contact with the medium to be analyzed, for example via a flow channel arranged on the support. A sensor having integrated flow channel is particularly suited for automation of the detection process or for long-term monitoring. However, direct contact with the sample medium can also be conceived by immersion or trickling.

The structure of the electrochemical sensor of the invention permits minimizing of the influence of interfering materials and hence cross-sensitivities in simple manner. This is possible in two ways. Firstly, an interference protective layer may be arranged between sample to be analyzed and the electrode which prevents entry of interfering materials into the support cavity by size and/or charge exclusion. Layers of this type may consist, for example of polymer layers of silicone, polytetrafluoroethylene, polyacrylate, polyurethane, cellulose acetate, Naflon, polycarbonate or polyvinyl chloride. They may line the support cavity completely or even partly, for example in the region of the support or cover opening.

A further possibility for reducing the effect of interfering materials consists in arranging a further electrode, preferably in the region of the support or cover opening, between the detection electrode and the sample to be analyzed and connecting to a voltage source. Interfering materials may be oxidized or reduced by applying a voltage to this electrode, resulting in it being possible to reduce cross-sensitivities. The further electrode is advantageously situated in the immediate vicinity of the detection electrode having inner surfaces and is electrically separated from the latter by an insulating layer or a thin gap.

The further electrode may be designed like the detection electrode, but wherein material-recognizing substance is not incorporated in the hollow cavities. This guarantees that interfering materials are reduced or oxidized at the surface of the further electrode on their path through the further electrode to the detection electrode with considerable probability.

Further positive properties and preferences of the invention can be seen from the exemplary embodiments described below and the figures.

Figure 1:
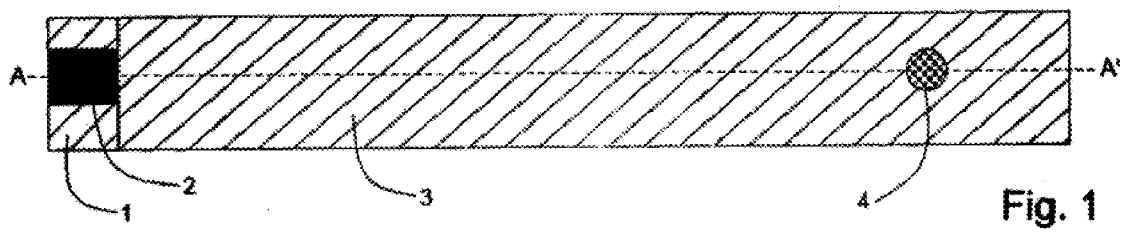
FIGS. 1, 2 show an electrochemical sensor (plan view and section A–A')
Figure 2:
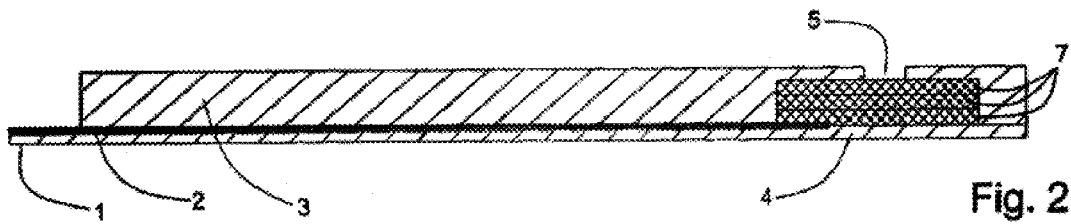

Glucose can be determined by way of example using the electrochemical sensor shown in FIG. 1 and FIG. 2. In this case a 250 μm thick laminating film made from polyethylene/polyester is used for the support 1. The leakage 2 consists of a carbon paste deposited on the support 1 by means of screen printing and extends into the electrode cavity 4. A metallised electrode made of three thin filter papers 7 of 3 mm diameter sputtered with platinum is situated in the electrode cavity 4. The individual layers are in surface electrical contact and in their entirety form the three-dimensional, irregularly reticulated electrode. The cover 3 consists of a 60 μm thick laminating film made from polyethylene/polyester, which is permeable to oxygen over the entire surface area, whereas it is permeable to glucose only through the previously punched opening 5 having a diameter of 1 mm. The diffusion of glucose into the support cavity 4 is possible via this opening. The material-recognizing membrane consisting of a solution of glucose oxidase in a photo-crosslinkable polyvinyl alcohol gel, is introduced into the pores of the metallised electrode cavity 4 through the opening 5. Distribution of the membrane in the support cavity 4 is thus effected by capillary forces. The material-recognizing membrane is polymerized by UV radiation and thus rendered water-insoluble. The support cavity 4 is a reservoir for the material-recognizing membrane and thus extends the service life of the sensor.

Figure 14:
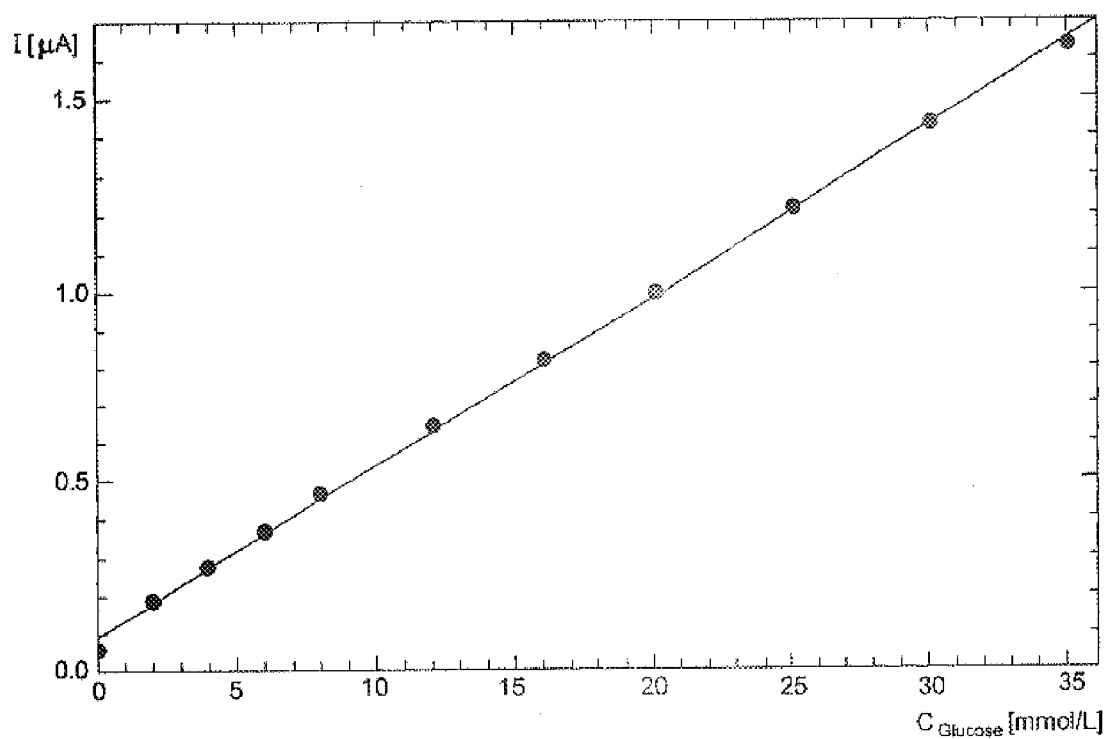
FIG. 14 shows the calibration curve of an electrochemical sensor of the invention having increased co-substrate permeability.

FIG. 14 shows the calibration curve of a sensor of this type. The good linearity, even for high glucose concentrations up to 35 mmole/liter, due to the improved co-substrate permeability can be seen clearly. For traditional sensors the end of the linear range lies at considerably lower glucose concentrations.

Determination of a number of other substances is possible using an electrochemical sensor of this type, in addition to glucose determination, wherein essentially the composition should be adapted to the material-recognizing membrane. Some examples are outlined in the following table:

| Analyte | Material-recognizing substance | Co-substrate | Detection |
| --- | --- | --- | --- |
| Cholesterol | Cholesterol oxidase | Oxygen | Hydrogen peroxide |
| Triglycerides | Esterase, glycerokinase, glycerophosphatoxidase | Oxygen | Hydrogen peroxide |
| Creatinine | Creatininase, creatinase, sacrosinoxidase | Oxygen | Hydrogen peroxide |
| Uric acid | Uricase | Oxygen | Hydrogen peroxide |

Figure 3:
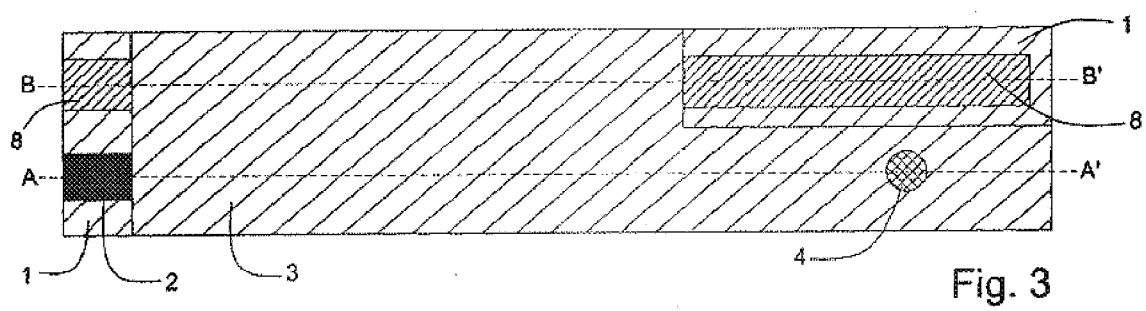
FIGS. 3, 4, 5 show an electrochemical sensor with integrated reference electrode (plan view, sections A–A' and B–B')
Figure 4:
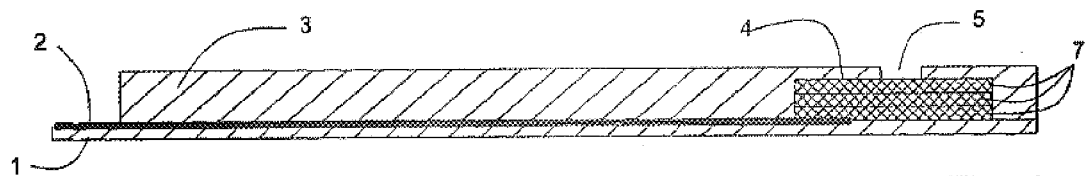
Figure 5:
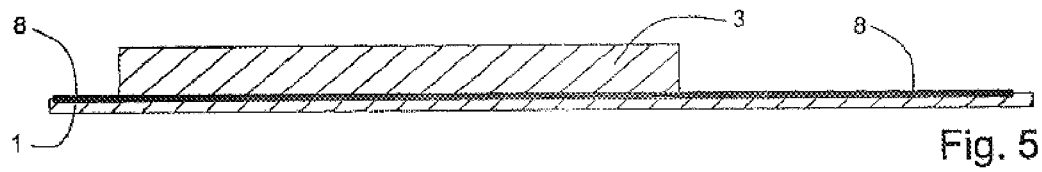

Integration of the counter-electrode 8 is shown in FIGS. 3, 4 and 5. In a double-electrode arrangement, the counter-electrode 8 also assumes the function of the reference electrode. A silver/silver chloride paste, which is applied to the support 1 by means of screen printing, serves as material for this.

Figure 6:
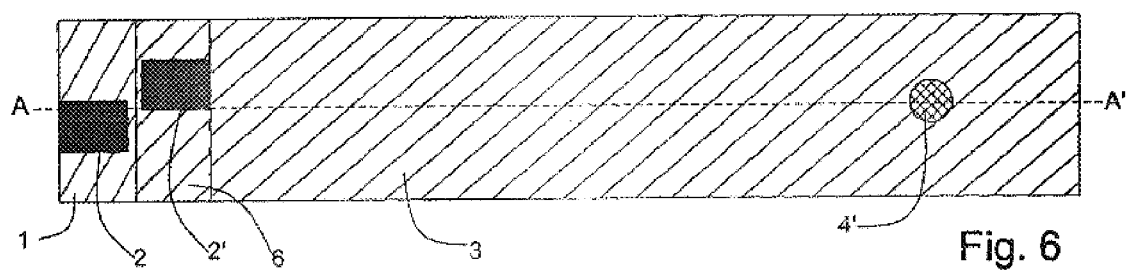
FIGS. 6, 7 show an electrochemical sensor with individual contact of the part electrodes (plan view and section A–A')
Figure 7:
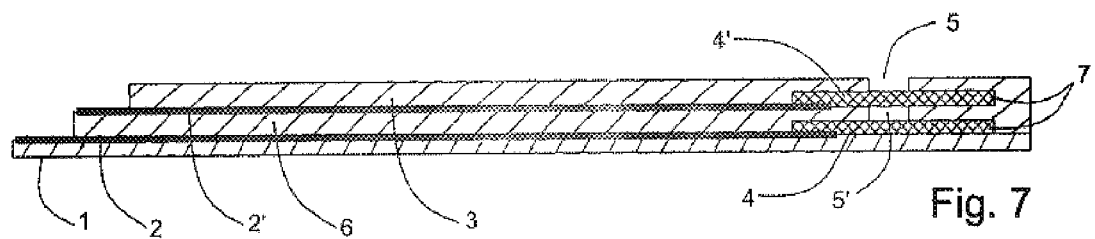

Contact of individual support cavities 4 and 4' by means of separate leakages 2 and 2' is shown as the next example of the invention in FIGS. 6 and 7. The leakages 2 and 2' are separated from one another by an insulating layer (spacer) 6.

The separated support cavities 4 and 4' are joined to one another by the opening 5' in the insulating layer 6. Two materials can be detected at the same time using this sensor configuration by introducing different material-recognizing membranes into the support cavities 4 and 4'.

In addition, there is the possibility of only filling the electrode in support cavity 4 with a material-recognizing membrane. For the example of glucose determination, the electrode incorporated in the support cavity 4' and connected to a voltage source then serves to oxidize oxidisable substances, such as ascorbic acid or uric acid, at 700 mV against a silver/silver chloride paste, so that they no longer interfere in the determination in the support cavity 4.

Figure 8:
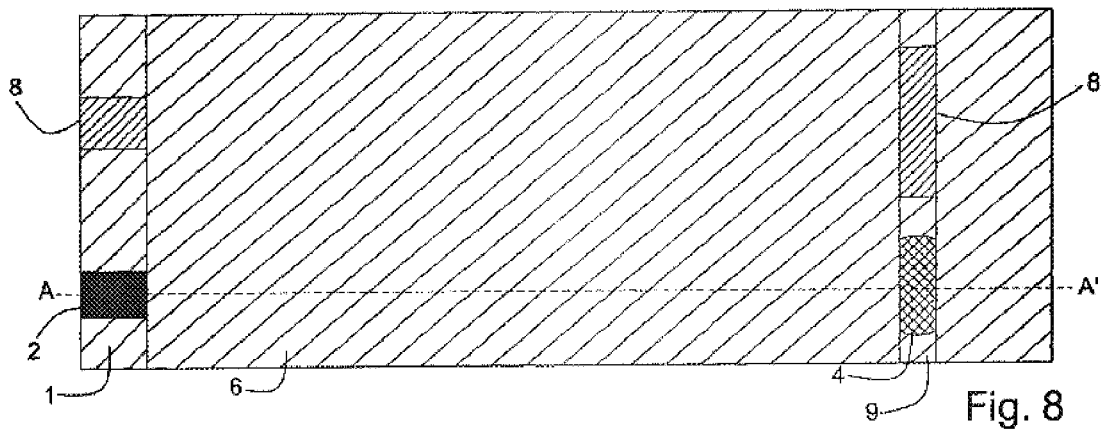
FIGS. 8, 9 show an electrochemical sensor with integrated reference electrode in through-flow arrangement (plan view and section A–A')
Figure 9:
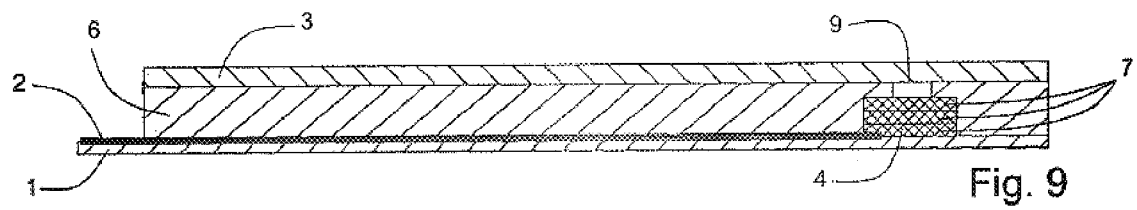

A further modification of the electrode is shown in FIGS. 8 and 9. A flow channel 9 is inserted here between the electrode cavity 4 or the reference electrode 8 and the cover 3, as a result of which adaptation of the sensor for through-flow measurements is facilitated without considerable expense.

Figure 10:
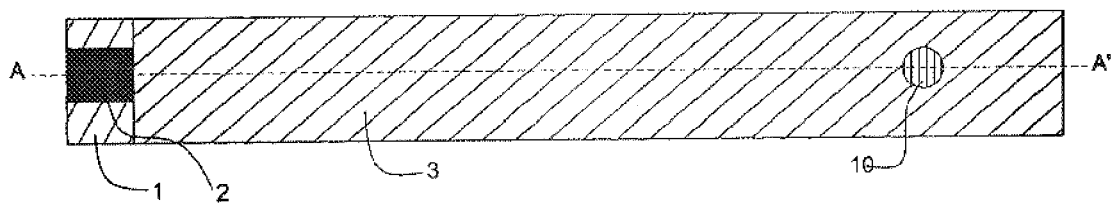
FIGS. 10, 11 show an electrochemical sensor with interference protective layer (plan view and section A–A')
Figure 11:
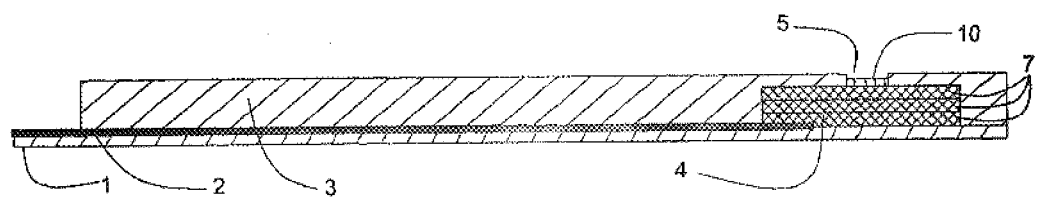

FIGS. 10 and 11 shows a further electrode of the invention, in which an interference protective layer is applied above the support cavity 4.

Figure 12:
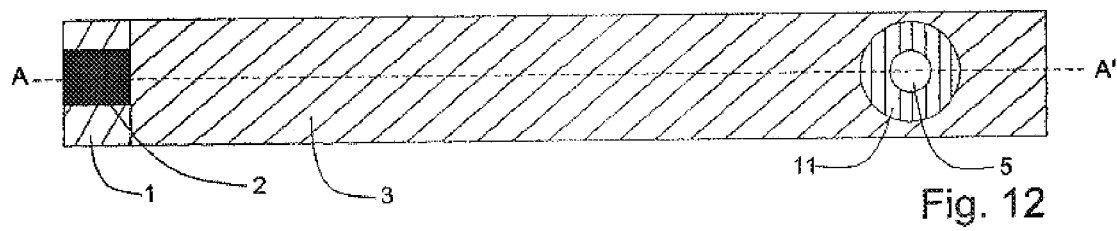
FIGS. 12, 13 show an electrochemical sensor with particularly high co-substrate permeability (plan view and section A–A')
Figure 13:
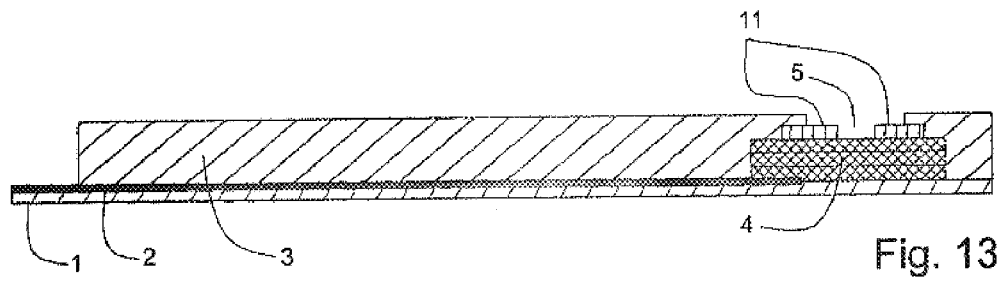

FIGS. 12 and 13 shows a further example of the sensor of the invention. A larger hole as the opening 5 of the support cavity 4 is punched in the cover 3 made from laminating film. The support cavity 4 is covered by a layer 11, which has a particularly high co-substrate permeability and in which the opening 5 is introduced. 30 μm thin silicone film, a material having very high oxygen permeability, is used here for the glucose sensor. Materials which cannot be melted or adhered particularly easily can also be used for the sensor structure in this manner.

What is claimed is:

1. Electrochemical sensor for determining material concentration comprising a support and an electrode arranged in a region of the support, wherein the electrode comprises a plurality of electrode layers arranged one above another, wherein two of the plurality of electrode layers each comprises a non-conductive parent substance, wherein the non-conductive parent substance of at least one electrode layer has inner hollow cavities within it, wherein at least some of a surface of the inner hollow cavities within the parent substance is coated with a layer of a conductor, and wherein a specific material-recognizing substance is incorporated into at least some of the inner hollow cavities within the non-conductive parent substance of at least one electrode layer.

2. Electrochemical sensor according to claim 1 wherein a spacer comprising an electrically insulating material is arranged between the electrode and another electrode.

3. Electrochemical sensor according to claim 2 wherein the two electrodes are provided with separate leakages.

4. Electrochemical sensor according to claim 1 wherein the non-conductive parent substance comprises an element selected from the group consisting of: paper, filter paper, paperboard, glass fibers, plastic fibers, textile, ceramic, mineral material, and material of vegetable or animal origin.

5. Electrochemical sensor according to claim 1 wherein the material-recognizing substance comprises an element selected from the group consisting of: enzymes, microbes, bacteria, and yeasts.

6. Electrochemical sensor according to claim 1 wherein the material-recognizing substance is immobilized with the aid of an element selected from the group consisting of: gel polymer, elasticized polymer, polyvinyl alcohol, polyvinyl chloride, polyurethane, acrylate, and silicone.

7. Electrochemical sensor according to claim 1 wherein the support comprises a cavity receiving at least one electrode layer.

8. Electrochemical sensor according to claim 7 wherein the support cavity is provided with a cover.

9. Electrochemical sensor according to claim 8 wherein the support and/or the cover is permeable to reaction-assisting or accompanying materials and is impermeable to a particular material to be determined.

10. Electrochemical sensor according to claim 8 wherein the support and/or the cover has at least one opening.

11. Electrochemical sensor according to claim 8 wherein the support and/or the cover comprises an element selected from the group consisting of: beat-sealing film, laminating film, self-adhesive film, and sealable film.

12. Electrochemical sensor according to claim 1, wherein a reference electrode and/or counter-electrode is arranged on the support.

13. Electrochemical sensor according to claim 12 wherein the electrode and the reference electrode and/or counter-electrode come into contact with a sample medium to be analyzed via a flow channel.

14. Electrochemical sensor according to claim 1 wherein an interference protective layer is arranged between a sample medium to be analyzed and an electrode layer.

15. Electrochemical sensor according to claim 14 wherein the interference protective layer comprises an element selected from the group consisting of: polymer layer of silicone, polytetrafluoroethylene, polyacrylate, polyurethane, cellulose acetate, perfluorinated membrane, polycarbonate, and polyvinyl chloride.

16. Electrochemical sensor according to claim 1 further comprising another electrode connected to a voltage source and arranged between a sample medium to be analyzed and at least one electrode layer.

17. Electrochemical sensor according to claim 16 wherein the support comprises a cavity receiving at least one electrode layer, wherein the support cavity is provided with a cover, wherein the cover has at least one opening, and wherein the received electrode layer is arranged in a region of the opening of the cover.

18. Electrochemical sensor according to claim 1 wherein the support comprises a cavity receiving at least one electrode layer, wherein the support cavity is provided with a cover, wherein the material-recognizing substance contains glucose oxidase for determining glucose, and wherein the support or the cover is permeable to oxygen.

19. Electrochemical sensor according to claim 1 wherein the conductor comprises an element selected from the group consisting of: platinum, silver, gold, and carbon.

* * * * *